United States Patent
Satou et al.

(10) Patent No.: US 7,361,780 B2
(45) Date of Patent: Apr. 22, 2008

(54) APPARATUS FOR PRODUCING HYDROXYALKYL(METH)ACRYLATE AND PROCESS FOR PRODUCING THE SAME

(75) Inventors: Yoshihiko Satou, Saeki-gun (JP); Katsunari Shigemune, Otake (JP); Junichi Doi, Hatsukaichi (JP); Yasuhiro Kabu, Saeki-gun (JP); Nobuo Ooya, Osaka (JP)

(73) Assignees: Mitsubishi Rayon Co., Ltd., Tokyo (JP); Osaka Organic Chemical Ind., Ltd., Osaka-shi (JP)

( * ) Notice: Subject to any disclaimer, the term of this patent is extended or adjusted under 35 U.S.C. 154(b) by 0 days.

(21) Appl. No.: 10/542,913

(22) PCT Filed: Jan. 30, 2004

(86) PCT No.: PCT/JP2004/000911

§ 371 (c)(1),
(2), (4) Date: Dec. 30, 2005

(87) PCT Pub. No.: WO2004/067491

PCT Pub. Date: Aug. 12, 2004

(65) Prior Publication Data
US 2006/0167304 A1    Jul. 27, 2006

(30) Foreign Application Priority Data
Jan. 31, 2003   (JP)   ............... 2003-023441

(51) Int. Cl.
*C07C 67/26* (2006.01)
*B01J 8/08* (2006.01)

(52) U.S. Cl. ...................... 560/209; 422/232

(58) Field of Classification Search ............ None
See application file for complete search history.

(56) References Cited

U.S. PATENT DOCUMENTS 4,449,544 A * 5/1984 Soderberg ............... 137/15.04
5,308,366 A * 5/1994 Stelman ..................... 48/61

FOREIGN PATENT DOCUMENTS

| JP | 59-122470 | 8/1984 |
| JP | 5-8141 | 2/1993 |
| JP | 2002-234861 | 8/2002 |

OTHER PUBLICATIONS

Bingxuan Wang, "Development of Ball Discharging Valve for Use in Kettle", Chemical Process Equipment & Piping, 1991., No. 2, pp. 58-61.

* cited by examiner

*Primary Examiner*—Paul A. Zucker
(74) *Attorney, Agent, or Firm*—Oblon, Spivak, McClelland, Maier & Neustadt, P.C.

(57) ABSTRACT

The present invention provides an apparatus for producing hydroxyalkyl(meth)acrylate and method for producing hydroxyalkyl(meth)acrylate, which can maintain high sealing performance even if the maintenance frequency of the blowdown valve is reduced. The apparatus for producing hydroxyalkyl(meth)acrylate of the present invention has a reaction vessel for synthesizing hydroxyalkyl(meth)acrylate, which has a blowdown valve placed in the reaction vessel, and the blowdown valve is opened when discharging contents of the reaction vessel and is a ball valve. The method of producing hydroxyalkyl(meth)acrylate of the present invention involves producing hydroxyalkyl(meth)acrylate using the aforementioned apparatus for producing hydroxyalkyl(meth)acrylate.

4 Claims, 3 Drawing Sheets

APPARATUS FOR PRODUCING HYDROXYALKYL(METH)ACRYLATE AND PROCESS FOR PRODUCING THE SAME

TECHNICAL FIELD

The present invention relates to an apparatus for producing hydroxyalkyl(meth)acrylate and a method of producing the same. More particularly, the present invention relates to a blowdown valve, which is placed at the bottom of a reaction vessel and is opened when discharging contents of the reaction vessel.

Priority is claimed on Japanese patent application No.2003-23441, the content of which is incorporated herein by reference.

BACKGROUND ART

Conventionally, hydroxyalkyl(meth)acrylate is, in general, synthesized by reacting (meth)acrylic acid and an excess amount of alkylene oxide as raw materials under elevated pressure at a temperature of from 40 to 70° C. in a reaction vessel in the presence of a catalyst or a polymerization inhibitor. Following the synthesis, the reaction mixture which has been produced in the reaction vessel is transferred to a deaerator, a distillation apparatus, by increasing the pressure of the reaction vessel, opening the upper part to be under the atmospheric pressure, or using a pump, to obtain a high-purified hydroxyalkyl(meth)acrylate.

The reaction vessel used for producing such hydroxyalkyl (meth)acrylate has a blowdown valve, which is opened when discharging contents. In general, a flush valve is used as the blowdown valve, because it prevents the formation of a liquid pool in the reaction vessel.

FIG. 3 shows an example of a cross-sectional view of a flush valve. This flush valve 20 has a valve body 22 forming a passage 21, a valve rod 23 which is inserted in the passage 21 of the valve body 22 and can move up and down, a valve head 26 which is disposed on the top of the valve rod 23, and a valve seat 25 which is disposed in the passage 21 and contacts the valve head 26 when the valve rod 23 is taken down. A blowdown aperture 24 is disposed obliquely downward at the lower part of valve body 22.

In such flush valve 20, when the valve head 26 contacts the valve seat 25, the passage is blocked to stop a flow and when the valve rod 23 moves upward and the valve head 26 is separated from the valve seat 25, the passage is opened.

However, a synthetic reaction of hydroxyalkyl(meth)acrylate may produce, as by-product, diesters derived from a reaction of hydroxyalkyl(meth)acrylate with (meth)acrylic acid or dialkylene glycol monoesters derived from a reaction of hydroxyalkyl(meth)acrylate with alkylene oxide.

The hydroxyalkyl(meth)acrylate as an objective product and the aforementioned by-product are very easily polymerized, compared with other alkyl(meth)acrylate. Accordingly, polymerization inhibitor solution, which contains polymerization inhibitor such as a phenol compound, a paraphenylenediamine compound, an amine compound, a copper dialkyldithiocarbamate, or a N-oxyl compound, is added to the reaction vessel. However, in a conventional adding method, because the polymerization inhibitor solution does not contact a cover part, an upper part, or the like of the reaction vessel, vapor of hydroxyalkyl(meth)acrylate, which contacts the cover part or the upper part, may polymerize to produce a polymer called "popcorn".

Furthermore, an addition reaction using ethylene oxide such as a synthesis of hydroxyalkyl (meth)acrylate is common to be continuously performed without cleaning the inside of the reaction vessel after transferring the reaction mixture in order to avoid impurities and improve its productivity. When the reaction is continuously carried out over a long term, an amount of the produced polymer continues to increase gradually. A part of the polymer sometimes comes off intermittently and floats in the reaction mixture.

If the polymer floats in the reaction mixture, the polymer may get stuck to the valve head or the valve rod when opening the flush valve and discharging the reaction mixture, meaning not all of the polymer is discharged and a part of the polymer remains at the bottom of the reaction vessel. In this case, when the valve rod is taken down with the polymer remaining at the bottom and the flush valve is closed, the remaining polymer may be sandwiched between contacting surfaces of the valve head and valve seat (seal surface) and degrade sealing.

In general, when a (meth)acryl ester is produced by an esterification reaction, transesterification reaction, addition reaction, or the like, (meth)acrylic acid or its ester, and an alcohol which have low toxicity and low explosiveness are used as main raw materials and thus high sealing performance is not required. However, when using alkylene oxide, which has high toxicity and high explosiveness, in such as a production of hydroxyalkyl(meth)acrylate, high sealing performance is required. For fulfilling the requirement, in production of hydroxyalkyl(meth)acrylate, the continuous production is interrupted and maintenance for removing the remaining polymer at the bottom of the reaction vessel is performed. As a result, productivity is not sufficiently high.

A method of maintaining high sealing performance of a flush valve is discussed and, for example, Japanese Utility Model Laid-Open Application No. Hei 5-8141 (FIG. 1) suggests using a valve seat for a blowdown valve of a container bottom without leaking a mixture from a reaction vessel.

However, when polymers flow in the reaction mixture, even if a flush valve has the valve seat for a blowdown valve of a container bottom described in Utility Model Laid-Open Application No. Hei 5-8141, a small amount of the polymer remains in the reaction vessel, and thus it is not possible to sufficiently prevent polymer from being sandwiched between the seal surfaces. Therefore, high sealing performance cannot be maintained.

DISCLOSURE OF INVENTION

The present invention has been made in view of the above-mentioned disadvantages and an object of the present invention is to provide an apparatus for producing hydroxyalkyl(meth)acrylate and a method of producing the same, which can maintain high sealing performance even if maintenance frequency of the blowdown valve is reduced.

As a result of extensive studies to solve the aforementioned problems, the following apparatus for producing hydroxyalkyl(meth)acrylate and a method of producing the same have been invented.

That is, the apparatus for producing a hydroxyalkyl(meth) acrylate of the present invention is characterized by having a reaction vessel for synthesizing hydroxyalkyl(meth)acrylate and a blowdown valve, which is placed in the reaction vessel and is opened when discharging contents of the reaction vessel, in which the blowdown valve is a ball valve.

According to the apparatus for producing hydroxyalkyl (meth)acrylate of the present invention, it is preferable that the hydroxyalkyl(meth)acrylate is hydroxyethyl(meth)acrylate.

The method of producing hydroxyalkyl(meth)acrylate of the present invention is characterized by producing the hydroxyalkyl(meth)acrylate using the aforementioned apparatus for producing hydroxyalkyl(meth)acrylate.

BEST MODE FOR CARRYING OUT THE INVENTION

Figure 1:
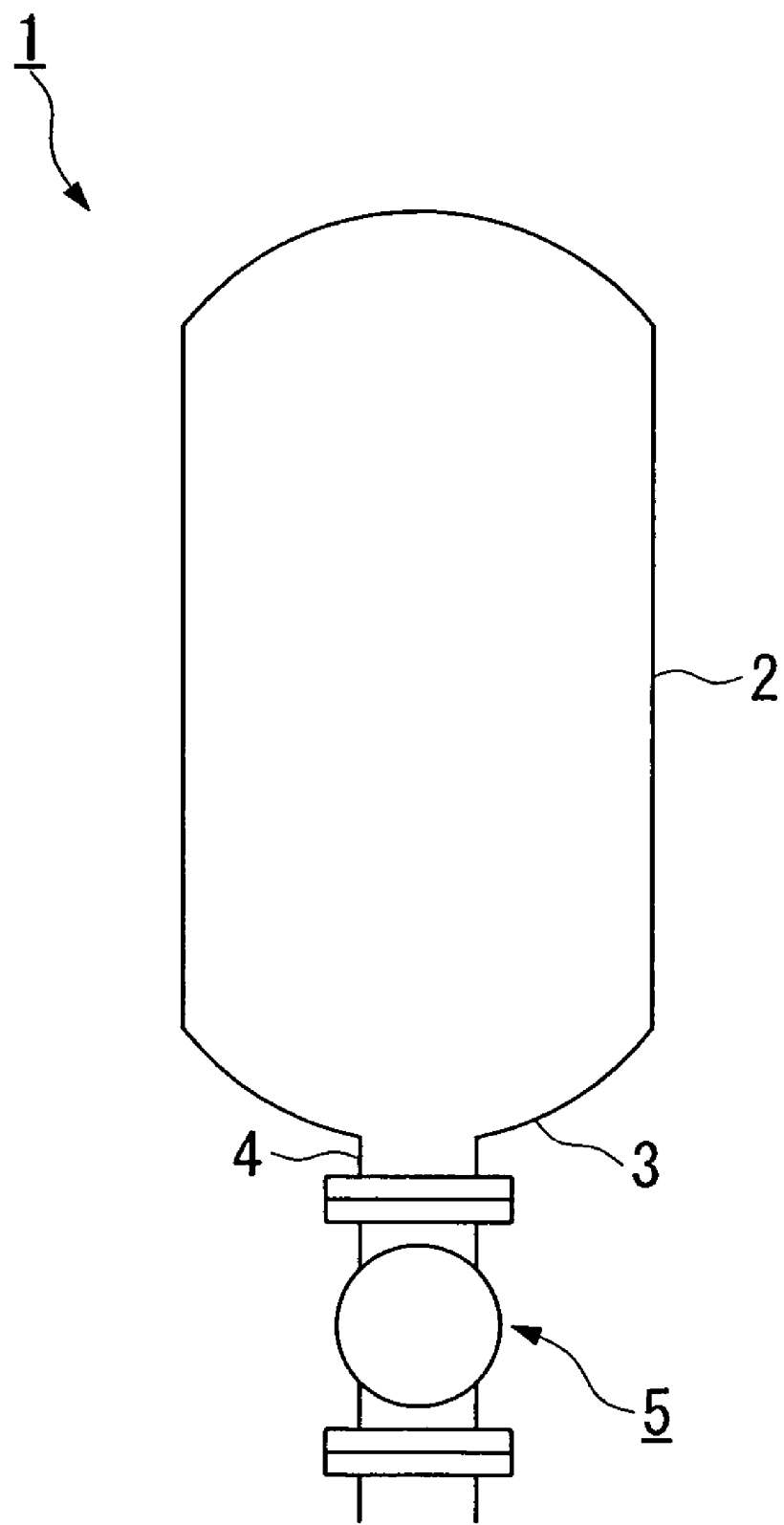
FIG. 1 is a side view to show an embodiment of an apparatus for producing hydroxyalkyl(meth)acrylate of the present invention.

An embodiment of the apparatus for producing hydroxyalkyl(meth)acrylate (hereinafter called producing apparatus) of the present invention is explained referring to FIG. 1.

This producing apparatus 1 has a reaction vessel 2 for synthesizing hydroxyalkyl(meth)acrylate and a ball valve 5 as blowdown valve which is placed through a conduit 4 at the bottom 3 of a reaction vessel 2 and is opened when discharging the contents of the reaction vessel.

Figure 2A:
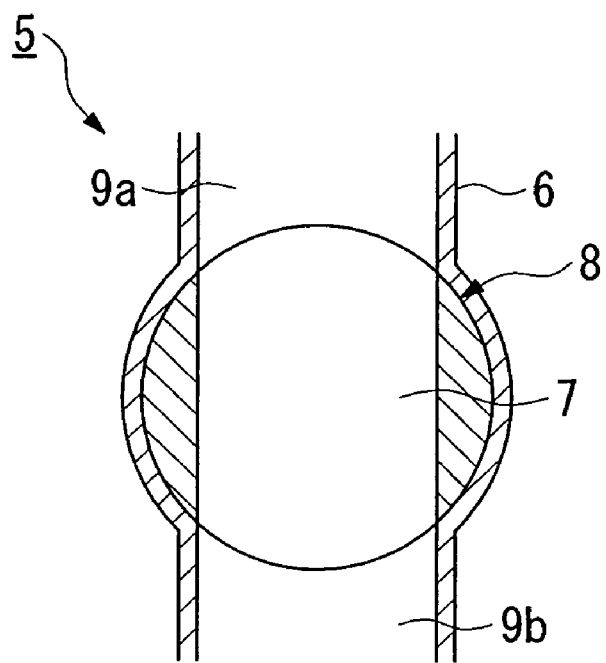
FIGS. 2A and 2B are cross-sectional views of a ball valve to compose an embodiment of an apparatus for producing hydroxyalkyl(meth)acrylate of the present invention, in which 2A is a view when the ball valve is fully opened and 2B is a view when the ball valve is fully closed.
Figure 2B:
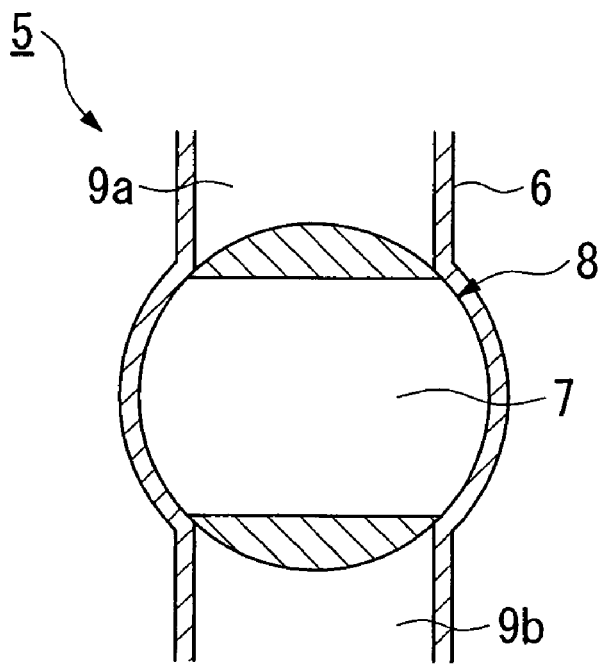
Figure 3:
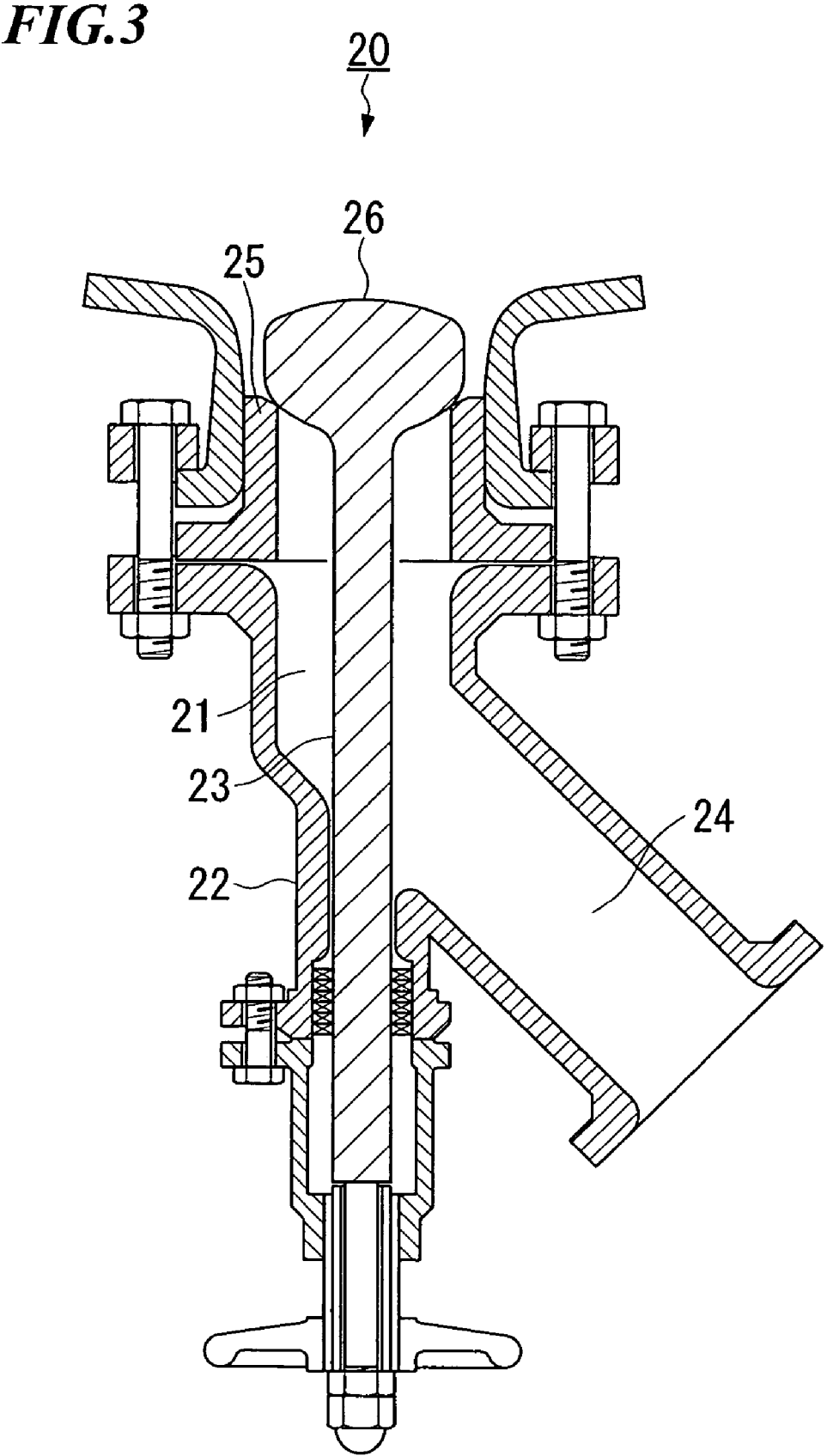
FIG. 3 is a cross-sectional view of an example of a flush valve.

The ball valve 5, as shown in FIG. 2A, has a ball 8 which is placed in a tubular valve body 6, is round, is rotatable, and has a through-hole 7, and a part of an inner surface of the valve body 6 and a part of an outer surface of the ball 8 contact each other closely. This ball valve 5 is open when the ball 8 is disposed with the through-hole 7 in communication with the passage 9a and 9b in the valve body 6 and is closed as shown in FIG. 2B when the ball 8 is disposed as a surface which does not have the through-hole 7 blocking the passage 9a and 9b in the valve body 6. The ball 8 of the ball valve 5 is rotated by driving means not shown in the figure.

It is preferable that the inner diameter of the through-hole 7 is almost the same as the inner diameter of the passage 9a and 9b in the valve body 6. If the inner diameter of through-hole 7 is almost the same as the inner diameter of the passage 9a and 9b in the valve body 6, it is possible to prevent the polymer from blocking the through-hole 7.

It is preferable for the ball valve 5 to be placed as close to the reaction vessel 2 as possible. If the ball valve 5 is placed close to the reaction vessel 2, a mixture pool in the reaction vessel 2 will be small.

It is preferable that the conduit 4 from the reaction vessel 2 to the ball valve 5 is extended vertically to prevent blocking by the polymer. If the conduit 4 is curve-shaped, it is possible that the polymer will block the passage.

The following is a description of the method of producing hydroxyalkyl(meth)acrylate using the aforementioned producing apparatus (hereinafter called producing method). The producing method can be any method, provided hydroxyalkyl(meth)acrylate is produced by reacting (meth)acrylic acid and alkylene oxide in the reaction vessel 2. A general method is given as an example as follows. That is, the ball valve 5, which is placed at the bottom of the reaction vessel 3, is fully closed and (meth)acrylic acid, alkylene oxide in excess of the (meth)acrylic acid, and a catalyst are prepared in the reaction vessel 2. Next they are reacted under elevated pressure to obtain a reaction mixture including hydroxyalkyl(meth)acrylate, and remaining alkylene oxide in the reaction mixture is subsequently removed by vacuum deaeration treatment. Subsequently, the ball valve 5 is fully opened and the reaction mixture is transferred to a purification apparatus and purified by distillation and so on to obtain high-purity hydroxyalkyl(meth)acrylate. After discharging, the ball valve is fully closed again in preparation for the next reaction.

There are no particular restrictions on the hydroxyalkyl (meth)acrylate produced by the producing apparatus and the producing method and, for example, hydroxyatkyl(meth) acrylate includes hydroxyethyl(meth)acrylate, hydroxypropyl(meth)acrylate, and the like. It is especially preferable that hydroxyalkyl(meth)acrylate be the hydroxyethyl(meth) acrylate in the present invention, because the amount of production thereof is usually large and the effects of the present invention are of great use in this case.

In the above described producing apparatus and producing method, if a polymer such as "popcorn" or the like, which is formed at the cover part or the upper part of the reaction vessel 2, comes off to be mixed in the reaction mixture, the polymer easily flows with the reaction mixture and does not block the valve because the blowdown valve is a ball valve 5. Therefore, because it is possible to prevent the polymer from being sandwiched between the seal surfaces, high sealing performance can be kept over a long term and productivity is not reduced even if the maintenance frequency of the blowdown valve is reduced. In addition, the present invention is extremely useful in both industrial and environmental consideration, because leaking of alkylene oxide is prevented.

Following is a concrete description of the present invention based on a series of examples, although the invention is in no way restricted to the examples presented below.

EXAMPLE

In a reaction vessel for producing hydroxyethyl methacrylate (volume of 5 m$^3$), to which a ball valve was placed as a blowdown valve at the bottom of the reaction vessel, 34 kmol of methacrylic acid, 38 kmol of ethylene oxide, and 0.15 kmol of iron methacrylate as a catalyst were prepared and were reacted at 60° C. Subsequently, after a vacuum deaeration treatment in the reaction vessel was performed, the ball valve was fully opened and the reaction mixture was transferred to a purification apparatus to obtain high-purified hydroxyethyl methacrylate. In this case, a pressure applied to the ball valve was a maximum of 400 kPa (gage pressure) and a minimum of 2.0 kPa (absolute pressure).

The degree of sealing was evaluated at intervals of seven days, wherein a pressure of 400 kPa was applied to a primary side of the ball valve and soap water was applied on a secondary side of the ball valve. As a result, leakage was not found even after reactions of 880 batches had been continuously carried out. In other words, high sealing performance remained without maintenance.

Comparative Example

A hydroxyethyl methacrylate was produced in the same way as in the Example, except that a flush valve was substituted for the ball valve as a blowdown valve. As the result, because leakage was found in the seventieth batch in a continuous run, the run was restarted after maintenance. However, because leakage was found again in the 196$^{th}$ batch after restarting, the run was restarted again after maintenance. Furthermore, because leakage was found in the 105$^{th}$ batch again after restarting, maintenance was performed. As shown above, the frequency of maintenance was high and the productivity was reduced.

Reference Example

In a reaction vessel (volume of 15 m$^3$), to which a flush valve was placed as a blowdown valve at the bottom of the reaction vessel, 44 kmol of butanol, 75 kmol of methyl methacrylate, and 0.03 kmol of tetrabutoxy titanium as a catalyst were prepared and were reacted at 100 to 130° C. to obtain butyl methacrylate (BMA). In this case, leakage was not found at the flush valve even after reactions of 1600 batches had been continuously carried out.

INDUSTRIAL APPLICABILITY

According to the present invention, because it is possible to prevent polymers of hydroxyalkyl(meth)acrylate from being sandwiched between seal surfaces, high sealing performance can be maintained even if the maintenance frequency of the blowdown valve is reduced. Furthermore, it is preferable that the hydroxyalkyl(meth)acrylate is hydroxyethyl(meth)acrylate in the present invention.

The invention claimed is:

1. A method for producing hydroxyalkyl(meth)acrylate, comprising:

reacting (meth)acrylic acid and an alkylene oxide in a reaction vessel that is equipped with a blowdown ball valve to produce a hydroxyalkyl(meth)acrylate; and at the conclusion of the reaction, opening the blowdown ball valve in order to discharge the product produced from the reactor.

2. The method of producing hydroxyalkyl(meth)acrylate of claim 1, wherein the hydroxyalkyl(meth)acrylate is hydroxyethyl(meth)acrylate.

3. The method of producing hydroxyalkyl(meth)acrylate of claim 1, wherein a conduit is located at the base of the reaction vessel.

4. The method of producing hydroxyalkyl(meth)acrylate of claim 3, wherein said ball valve is located in said conduit through which the contents of the reaction vessel are discharged.

* * * * *